United States Patent [19]
Tang et al.

[11] Patent Number: 6,161,237
[45] Date of Patent: Dec. 19, 2000

[54] PATIENT POSITIONING DEVICE FOR RADIATION THERAPY

[75] Inventors: Wen Thye Tang; Vince S. Hursh, both of Orange City, Iowa; Todd M. Hauger, Sioux Falls, S. Dak.

[73] Assignee: Med-Tec, Inc., Orange City, Iowa

[21] Appl. No.: 09/363,115

[22] Filed: Jul. 29, 1999

[51] Int. Cl.[7] ...................................................... A61B 6/04
[52] U.S. Cl. .................... 5/621; 5/601; 378/209
[58] Field of Search ................... 128/845, 870; 378/209; 5/601, 621, 622, 658

[56] References Cited

U.S. PATENT DOCUMENTS

| | | | |
|---|---|---|---|
| 5,370,117 | 12/1994 | McLaurin, Jr. | 5/622 |
| 5,537,454 | 7/1996 | Korver, II . | |
| 5,566,681 | 10/1996 | Manwaring et al. | 5/622 |
| 5,775,337 | 7/1998 | Hauger et al. . | |
| 5,806,116 | 9/1998 | Oliver et al. . | |
| 5,832,550 | 11/1998 | Hauger et al. . | |
| 5,848,449 | 12/1998 | Hauger et al. . | |
| 5,983,436 | 11/1999 | Vanek et al. | 5/621 |

*Primary Examiner*—Michael F. Trettel
*Attorney, Agent, or Firm*—Zarley, McKee, Thomte, Voorhees & Sease

[57] ABSTRACT

A device is provided for accurately and repeatedly positioning a patient on a treatment table. The device includes a tabletop with indexing notches along each side, and a lock bar releasably securable to the tabletop. The lock bar has opposite ends with a ball adapted to snap-fit into opposing pairs of the notches on each side of the table. A patient restraint member is mounted on the lock bar to extend over a portion of the patient's body so as to position the patient on the table.

27 Claims, 4 Drawing Sheets

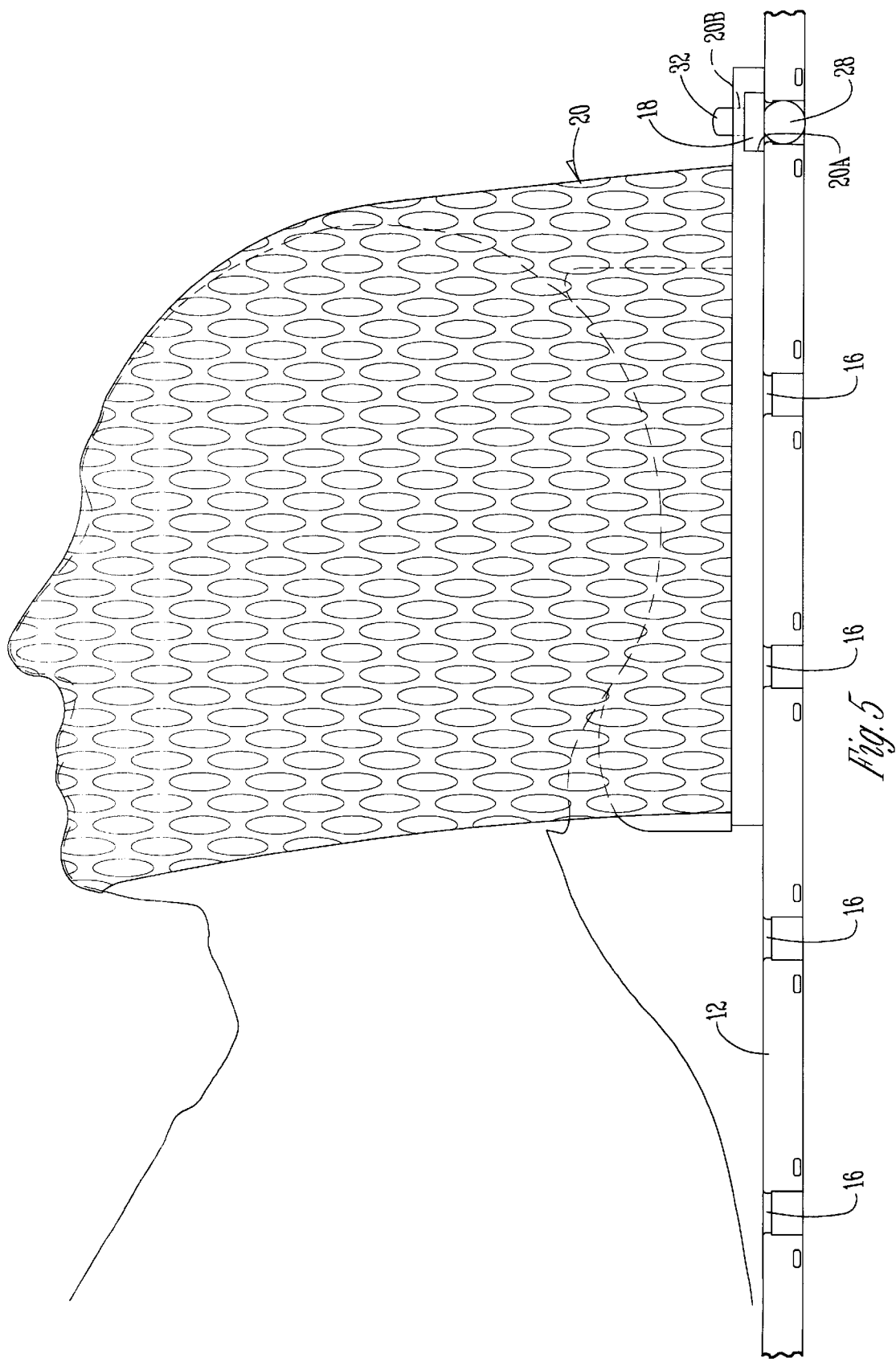

PATIENT POSITIONING DEVICE FOR RADIATION THERAPY

BACKGROUND OF THE INVENTION

Patient positioning systems are used for accurate and reproducible positioning of a patient for radiation therapy, diagnostic imaging, surgery, and other medical procedures. During these procedures, it is important to immobilize a part or parts of the patient's body. Accurate positioning of the body part is also important in repeat treatments so that the precise same location of the bodies are exposed to the radiation each time. Therefore, different types of devices have been made to immobilize body parts and to index the body to the treatment table to assure proper and repeatable alignment for radiation therapy.

One example of such a patient positioning system is the Exact Indexed Immobilization system sold by applicant, and described in U.S. Pat. No. 5,806,116. The Exact system utilizes a tabletop with indentations along opposite sides, and a lock bar extending across the tabletop with a disk at each end adapted to be received in opposing indentations. The Exact lock bar is secured to the tabletop with an eccentric cam which tightens the ends of the bar into engagement with the indentations of the tabletop.

While the Exact system is generally an acceptable product, there are features causing potential concern. For example, the rotation of the cam lever causes the bar to move slightly relative to the tabletop, such that the patient positioning is not precise and consistent. Also, the Exact lock bar utilizes an O-ring on each end of the bar, which is not resistant to radiation. Therefore, over time, the O-ring may degrade to a degree wherein the bar does not mount as securely to the tabletop. The O-ring may also ultimately fail due to repeated and extensive exposure to the radiation. Furthermore, the thermoplastic patient fixation or restraint devices normally used in patient positioning systems tend to shrink over time, as a result of the initial heating and molding of the thermoplastic. Such shrinkage ultimately may lead to bending of the Exact bar when the restraint is forced downwardly over the patient. Such bending of the bar may lead to migration of the bar out of the tabletop notches. Also, patient swelling may impart stresses on the Exact bar which may preclude secure attachment of the bar to the tabletop or Exact repeatable positioning of the bar.

Therefore, a primary objective of the present invention is the provision of an improved patient positioning system for radiation therapy treatment.

Another objective of the present invention is the provision of a patient positioning system which is repeatably precise and accurate.

Another objective of the present invention is the provision of a patient positioning system which provides secure interlocking connection between the lock bar and the tabletop.

A further objective of the present invention is the provision of a patient positioning system which is easy and simple to use.

Another objective of the present invention is the provision of a patient positioning system which is durable in use and economical to manufacture.

These and other objectives have become apparent from the following description of the invention.

SUMMARY OF THE INVENTION

The patient-positioning device of the present invention includes a table having opposite sides with indexing notches along each side. A patient restraint member is registered on an elongated lock bar and is adapted to extend over a portion of the patient's body to position the patient on the table. The lock bar has a downwardly extending ball on each end is adapted to snap-fit into opposing pairs of the notches on each side of the table. The notches each have a radius to matingly engage the ball, which is self centering in the notch. A shoulder in each notch retentively engages the ball to prevent relative movement between the lock bar and the table.

BRIEF DESCRIPTION OF THE DRAWINGS

FIG. 5 is a side elevation view showing the lock bar with a molded patient fixation device.

DETAILED DESCRIPTION OF INVENTION

Figure 1:
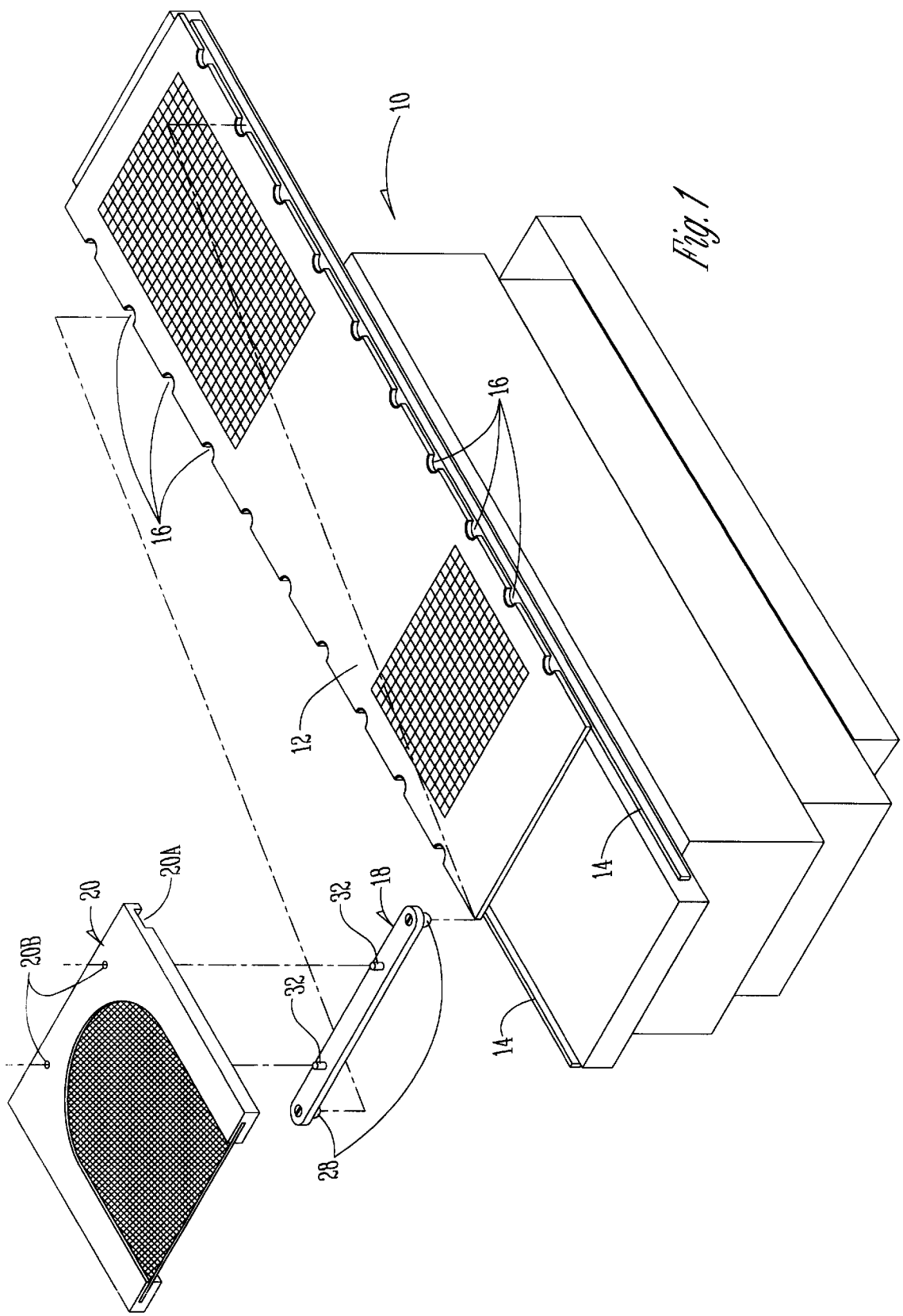
FIG. 1 is an exploded perspective view of the radiation therapy interlock system of the present invention, with a lock bar positioned above the tabletop and a patient fixation device before molding.
Figure 2:
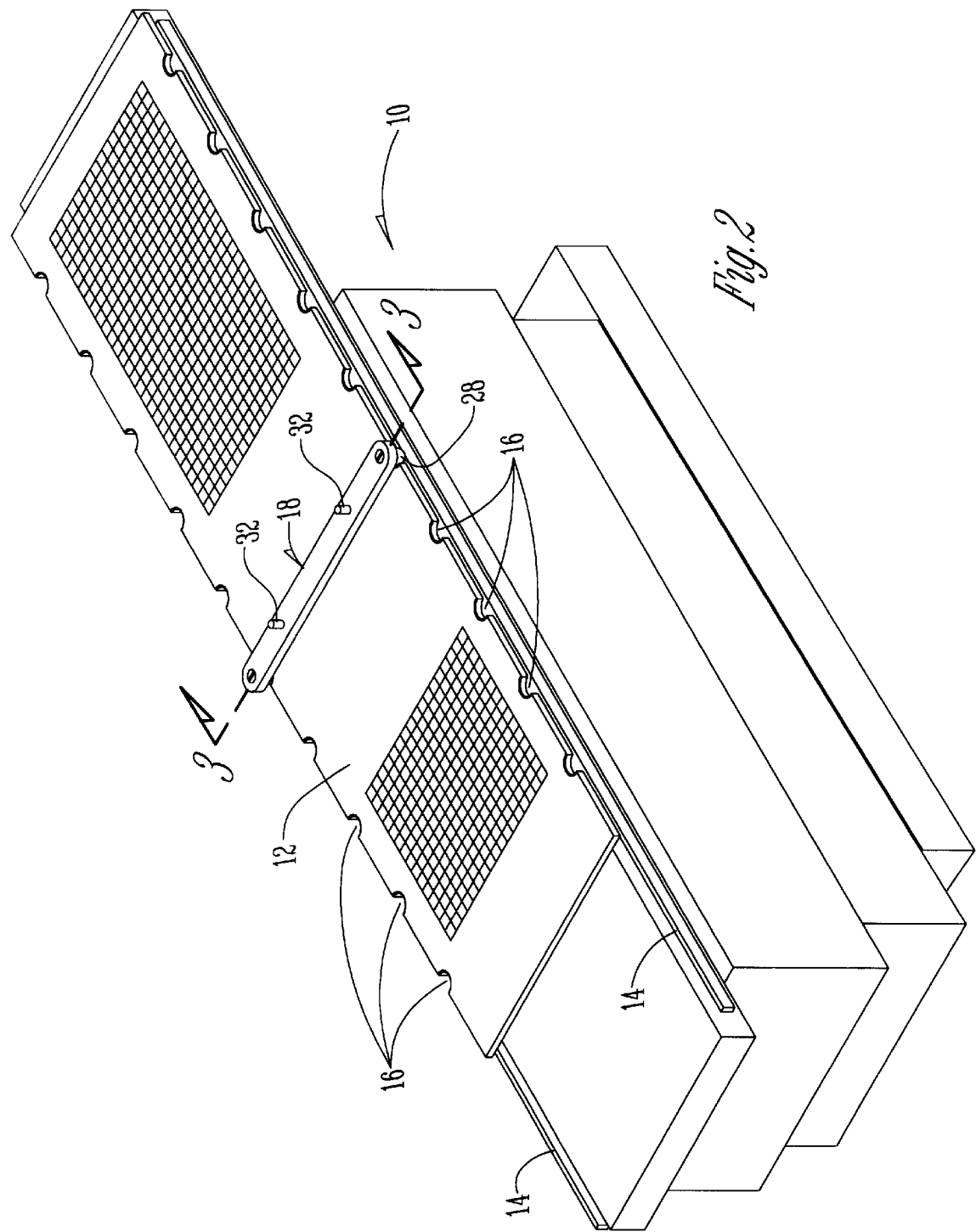
FIG. 2 is a view similar to FIG. 1 showing the lock bar snap-fit into position on the tabletop, with the patient restraint device removed for clarity.

The interlock system of the present invention is particularly useful for accurate and repeatable patient positioning for radiation therapy treatment, as well as for other diagnostic and treatment procedures. As seen in FIG. 1, a table base or carriage 10 is provided with a tabletop 12. The tabletop 12 is mounted for longitudinal movement upon side rails 14 attached to the opposite sides of carriage 10.

The tabletop 12 has a plurality of notches 16 along the opposite sides. The notches 16 are adapted to receive the opposite ends of a lock bar 18 to which a patient restraint member 20 is secured. The notches 16 serve as indexes for repeated treatments of individual patients.

Figure 4:
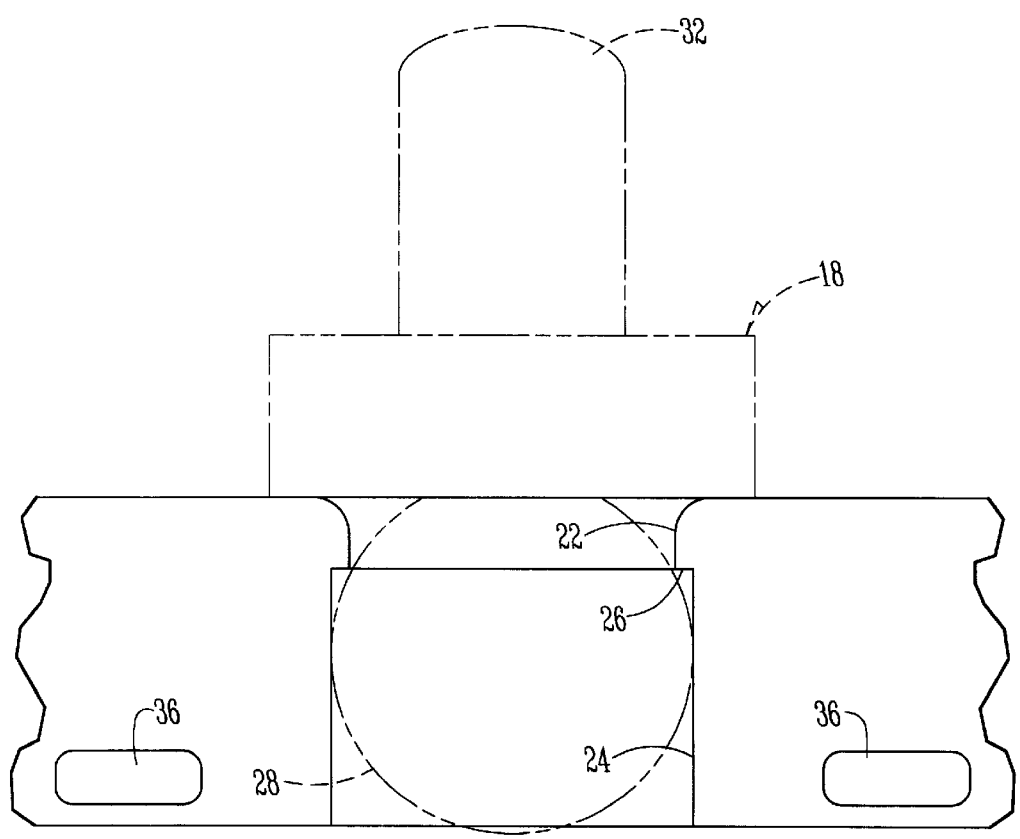
FIG. 4 is an enlarged side elevation view showing the lock bar snap-fit into position on the tabletop.

More particularly, as best seen in FIG. 4, each notch 22 extends through the tabletop 12, with an upper reduced diameter portion 22 and an enlarged diameter portion 24. The portions 22, 24 define a shoulder 26 in the notch 16.

Figure 3:
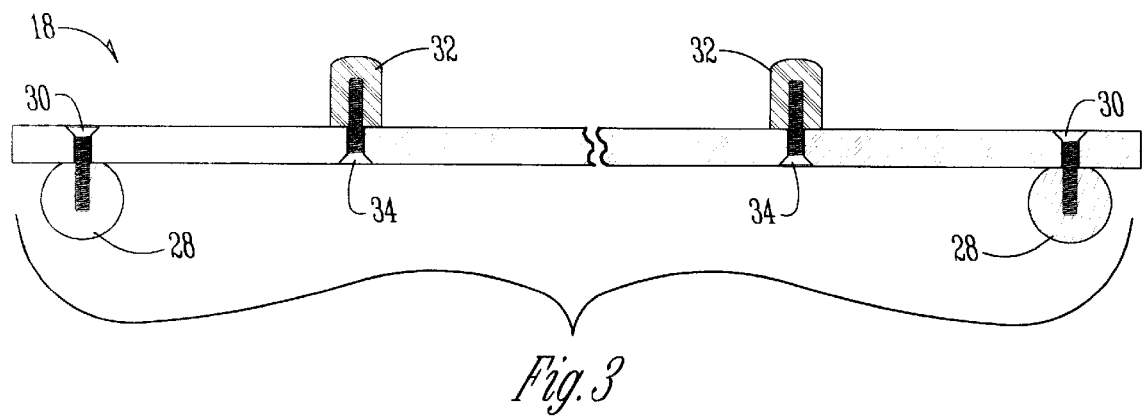
FIG. 3 is a sectional view of the lock bar taken along lines 3—3 of FIG. 2.

The lock bar 18 includes a male extension 28, preferably in the shape of a ball, a seen in FIG. 3. The ball 28 is connected to the lock bar 18 with a threaded bolt 30. It is understood that the male extension 28 of the lock bar 18 may take shapes other than spherical, as shown in the drawings, with the alternative shapes providing a snap-fit connection between the lock bar 18 and the notches 16 of the tabletop 12. The lock bar 18 also includes a pair of upwardly extending studs 32 which are secured to the bar 18 by bolts 34. The studs 32 are adapted to matingly register with holes 20B of the patient restraint device 20 so that the device 20 is positioned on the lock bar 18. The device 20 also has a bottom groove 20A sized to receive the bar 18.

In use, the lock bar 18 with the mounted patient restraint 20 is positioned over the patient. The balls 28 of the lock bar 18 are snap-fit into the desired opposing pairs of notches 16 in the tabletop 12 so as to secure the lock bar 18 to the table top 12. As seen in FIG. 4, the ball 28 is retentively engaged by the shoulder 26 of the notch 16, which is positioned above the mid point or equator of the ball 28. The ball 28 is also self-centering within the notch 16.

As seen in FIG. 4, the tabletop 12 also includes a pair of slots 36 on each side of each notch 16. If the eccentric cam action lock bar of U.S. Pat. No. 5,806,116 is used, the slots 36 accommodate the tab on the end of the lever arm thereof.

The preferred embodiment of the present invention has been set forth in the drawings, specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. A device for positioning a patient for treatment, comprising:
   a table for supporting the patient, the table having opposite sides with indexing notches along each side;
   a lock bar having opposite ends adapted to retentively engage opposing pairs of the notches on each side of the table; and
   a patient restraint member registered on the lock bar but without securement thereto;
   wherein the restraint member includes a slot for receiving the lock bar.

2. The device of claim 1 wherein the lock bar includes a plurality of pins and the restraint member includes apertures to receive the pins.

3. The device of claim 1 wherein the lock bar includes a plurality of pins and the restraint member includes apertures to receive the pins.

4. The device of claim 1 wherein the lock bar has a ball secured to each end, with the balls being adapted to snap fit into the opposing notches of the table.

5. A device for positioning a patient for treatment, comprising:
   a table for supporting the patient, the table having opposite sides with indexing notches along each side;
   a lock bar having opposite ends with a ball secured to each end, the balls being adapted to snap-fit into opposing pairs of the notches on each side of the table; and
   a patient restraint member on the bar and being adapted to extend over a portion of the patient's body to position the patient on the table.

6. The device of claim 5 wherein each notch has a radius to matingly engage the ball.

7. The device of claim 5 wherein each notch has a shoulder to retentively engage the ball.

8. The device of claim 5 wherein each notch has upper and lower ends, with the upper end having a smaller diameter than the lower end.

9. The device of claim 8 wherein the ball resides primarily in the lower end of the notch.

10. The device of claim 9 wherein the restraint member includes a slot for receiving the lock bar.

11. The device of claim 9 wherein the lock bar includes a plurality of pins and the restraint member includes apertures to receive the pins.

12. An improved patient positioning device for accurately and repeatedly positioning a patient on a table for treatment using a restraint member, the improvement comprising:
   a plurality of female indexing notches along opposite sides of the table;
   an elongated lock bar adapted to receive the restraint member and having non-pivotal male extensions on each end for snap-fit receipt in the notches so as to position the restraint member over the patient.

13. The device of claim 12 wherein the male extensions are substantially spherically shaped.

14. The device of claim 12 wherein the notches include a shoulder for retentively engaging the male extension.

15. The device of claim 12 wherein the notches and the male extension have varying dimension portions so as to provide the snap-fit.

16. The device of claim 12 wherein the notches and the male extensions each have a radius for mating engagement.

17. The device of claim 12 wherein the male extension is stationary relative to the bar.

18. The device of claim 12 wherein the male extensions are self-centering in the notches.

19. A method of restraining a patient on a treatment table, comprising:
   positioning the patient on the table;
   mounting a restraint member on a lock bar;
   extending the restraint member over the patient; and
   snap-fitting opposite ends of the lock bar vertically into indexing notches along each side of the table.

20. The method of claim 19 wherein the restraint member is registered on the lock bar without securement thereto.

21. A device for positioning a patient for treatment, comprising:
   a table for supporting the patient, the table having opposite sides with indexing notches along each side;
   a lock bar having opposite ends adapted to retentively engage opposing pairs of the notches on each side of the table;
   a patient restraint member registered on the lock bar but without securement thereto; and
   the lock bar including a plurality of pins and the restraint member includes apertures to receive the pins.

22. A device for positioning a patient for treatment, comprising:
   a table for supporting the patient, the table having opposite sides with indexing notches along each side;
   a lock bar having opposite ends adapted to retentively engage opposing pairs of the notches on each side of the table;
   a patient restraint member registered on the lock bar but without securement thereto; and
   the lock bar having a ball secured to each end, with the balls being adapted to snap fit into the opposing notches of the table.

23. The device of claim 22 wherein the restraint member includes a slot for receiving the lock bar.

24. The device of claim 22 wherein each notch has a radius to matingly engage the ball.

25. The device of claim 22 wherein each notch has a shoulder to retentively engage the ball.

26. The device of claim 22 wherein each notch has upper and lower ends, with the upper end having a smaller diameter than the lower end.

27. An improved patient positioning device for accurately and repeatedly positioning a patient on a table for treatment using a restraint member, the improvement comprising:
   a plurality of female indexing notches along opposite sides of the table;
   an elongated lock bar adapted to receive the restraint member and having substantially spherically shaped male extensions on each end for snap-fit receipt in the notches so as to position the restraint member over the patient.

* * * * *